(12) United States Patent
Plombon et al.

(10) Patent No.: US 7,050,851 B2
(45) Date of Patent: May 23, 2006

(54) IMPLANTABLE CARDIOVERTER/DEFIBRILLATOR WITH HOUSING ELECTRODE AND LEAD DETECTION AND SWITCHING CIRCUITRY

(75) Inventors: William J. Plombon, Coon Rapids, MN (US); John C. Stroebel, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 260 days.

(21) Appl. No.: 09/897,859

(22) Filed: Jun. 29, 2001

(65) Prior Publication Data
US 2003/0004552 A1    Jan. 2, 2003

(51) Int. Cl.
*A61N 1/37*  (2006.01)

(52) U.S. Cl. ............................................. 607/8; 607/28

(58) Field of Classification Search .............. 607/4–11, 607/27–28, 63, 1–2, 115–116; 600/547; 128/908
See application file for complete search history.

(56) References Cited

U.S. PATENT DOCUMENTS

| | | | |
|---|---|---|---|
| 5,003,975 A * | 4/1991 | Hafelfinger et al. .......... | 607/28 |
| 5,431,692 A | 7/1995 | Hansen et al. | |
| 5,447,521 A * | 9/1995 | Anderson et al. .............. | 607/5 |
| 5,534,018 A * | 7/1996 | Wahlstrand et al. .......... | 607/27 |
| 5,549,642 A | 8/1996 | Min et al. | |
| 5,549,646 A * | 8/1996 | Katz et al. ..................... | 607/8 |
| 5,607,455 A * | 3/1997 | Armstrong ..................... | 607/8 |
| 5,755,742 A | 5/1998 | Schuelke et al. | |
| 5,944,746 A * | 8/1999 | Kroll ............................ | 607/27 |
| 5,954,753 A * | 9/1999 | Alt et al. ....................... | 607/8 |
| 6,445,951 B1 * | 9/2002 | Mouchawar .................. | 607/28 |
| 6,473,645 B1 * | 10/2002 | Levine .......................... | 607/9 |
| 6,493,586 B1 * | 12/2002 | Stahmann et al. ............ | 607/27 |

FOREIGN PATENT DOCUMENTS

| | | |
|---|---|---|
| DE | 199 30 267 A1 | 1/2001 |
| WO | WO 96/37258 | 11/1996 |
| WO | WO 99/58192 | 11/1999 |

* cited by examiner

*Primary Examiner*—Robert E. Pezzuto
*Assistant Examiner*—Kristen Mullen
(74) *Attorney, Agent, or Firm*—Michael C. Soldner; Girma Wolde-Michael

(57) ABSTRACT

An implantable cardioverter/defibrillator includes an active can electrode and a high-voltage lead that can be electrically isolated from one another by opening a switch between them. The performance of the high-voltage lead and the can electrode can then be independently monitored, thus indicating which lead is inoperable, should one become inoperable. If a lead becomes inoperable, the implantable device can then reconfigure an electrical pathway such as a cardioversion and/or a defibrillation pathway by excluding the inoperable lead. By separating the high-voltage lead from the can electrode, pseudo ECG measurements can also be taken and utilized by the implantable device.

8 Claims, 6 Drawing Sheets

| | PROBLEMATIC ELECTRODE | | |
|---|---|---|---|
| MEASUREMENT | CAN | RV | SVC |
| SVC-CAN | OUT OF RANGE | IN RANGE | OUT OF RANGE |
| SVC-RV | IN RANGE | OUT OF RANGE | OUT OF RANGE |
| CAN-RV | OUT OF RANGE | OUT OF RANGE | IN RANGE |

FIG. 4

| MEASUREMENT | PROBLEMATIC ELECTRODE | | |
|---|---|---|---|
| | CAN | RV | SVC |
| SVC-CAN | OUT OF RANGE | IN RANGE | OUT OF RANGE |
| SVC-RV | IN RANGE | OUT OF RANGE | OUT OF RANGE |
| CAN-RV | OUT OF RANGE | OUT OF RANGE | IN RANGE |

IMPLANTABLE CARDIOVERTER/DEFIBRILLATOR WITH HOUSING ELECTRODE AND LEAD DETECTION AND SWITCHING CIRCUITRY

TECHNICAL FIELD

The present invention relates generally to implantable arrhythmia control devices and more specifically to implantable pacemakers, cardioverters and/or defibrillators.

BACKGROUND

Cardioversion generally refers to the discharge of relatively high energy electrical shocks into or across cardiac tissue to arrest a tachyarrhythmia of a cardiac chamber. The termination of high rate tachycardias with lesser energy electrical pulses or bursts has also been referred to as cardioversion. The arrest of atrial or ventricular fibrillation by higher energy shocks is referred to as defibrillation, and defibrillation has been characterized in the past as a form of cardioversion. Implantable cardioverter/defibrillator (ICD) systems are available for providing synchronous cardioversion shocks and/or asynchronous defibrillation shocks. Additionally, pacemaker/cardioverter/defibrillator (PCD) systems are available for providing additional staged therapies of anti-tachyarrhythmia pacing, synchronous cardioversion shocks and asynchronous defibrillation shocks.

ICD's or PCD's will typically include a housing assembly containing a microprocessor or control unit and a power supply. One or more leads are coupled to the housing assembly and positioned within or adjacent to a portion of the heart. The leads may include electrodes to deliver directed discharge of electrical current. The housing assembly itself can be formed from a conductive material and may serve as an electrode. When so utilized, the housing assembly is often referred to as an "active can" or can electrode. For example, an electrode may be positioned in the right ventricle (RV). A high voltage shock may then be directed from the can electrode to the RV electrode across a major portion of cardiac tissue. Of course, electrodes can be placed in any chamber of the heart and the defibrillating or cardioverting shock can be managed and administered as appropriate between various electrodes.

The variety of lead/electrode configurations available on ICD's or PCD allow for a wide range of treatment options directed specifically to a patient's particular cardiac condition. This variety also requires that certain common assemblies be implemented for use in varying contexts and programmabilities to accommodate specific configurations. In addition, it is desirable to determine the operative and functional status of the various components.

Certain implantable medical devices have previously performed some self diagnostic procedures. For example, commonly assigned U.S. Pat. No. 5,755,742 discloses a system that indirectly measures the impedance of certain leads coupled to an implantable pacemaker/cardioverter/defibrillator. A low voltage or sub-threshold pulse is generated across a given pair of leads. Another pair of leads then monitors that pulse and derives the impedance from the measured values. One lead is common to both the generating lead pair and the measuring lead pair. The derived impedances are used to assess and evaluate the integrity of the lead being tested.

SUMMARY

In general, the invention relates to an implantable PCD or ICD having a housing assembly that can be selectively set to an active can status. In addition, the PCD or ICD of the invention includes at least a first lead coupled to a high-voltage electrode, typically positionable in the superior vena cava (SVC). Also provided is second electrode which is typically an RV electrode positionable within the right ventricle of the heart and coupled with an RV lead.

An implantable PCD may include control circuitry coupled to the various leads and electrodes. Conventionally, when an SVC electrode and an active can electrode are provided on the same device, they are electrically connected together. Thus, the control circuitry cannot distinguish between the can electrode and the SVC electrode. The present invention enables the SVC electrode to be monitored and utilized independently of the can electrode, providing several features and improved device performance.

In some embodiments, the SVC electrode may not be implanted with the PCD or ICD. Instead, the SVC electrode may be implanted at a later time, and electrically coupled to an implanted PCD or ICD. The controller may be configured to monitor whether or not the SVC lead and electrode are electrically coupled to the PCD or ICD. When it is not detected, the controller disables the various functions that require the SVC electrode. Once the SVC electrode is detected, the controller enables those functions.

Once detected, the controller monitors the SVC lead and electrode, as well as other leads coupled to the PCD or ICD, to verify that they are operating within certain predetermined parameters. In particular, the controller may generate a low voltage or subthreshold pulse at predetermined time intervals, and monitors the impedance through the various leads. If the impedance falls within a predetermined range of values, the controller determines that the lead is operable. If not, the lead may be classified as problematic and an appropriate action may be taken. One such action would be to generate an alarm or alert that would indicate to the patient that a problem exists. Another action would be to reconfigure the defibrillation and/or cardioversion pathways. For example, a good but previously unused electrode may be utilized instead of the "malfunctioning" or inoperable lead.

In order to initially determine if the SVC lead is present and to monitor its performance after it is so detected, the SVC lead should be electrically separable from the can electrode. The present invention generally discloses a switch between the can electrode and the SVC electrode so as to selectively electrically decouple them. The switch is preferably operable by the controller and selectively opens and closes the connection between the can electrode and the SVC electrode. When the switch is opened, the impedance of the can electrode and the SVC electrode can be independently measured and monitored. In the alternative, if the switch is closed, the can electrode and the SVC electrode would be electrically coupled to one another.

When the switch is open, measurements of electrical cardiac activity between the can electrode and the SVC electrode can result in a pseudo ECG. The ECG is a "pseudo" ECG in the sense that it is measured internally, via the implantable medical device rather than externally through a conventional reading of ECGs. The ECG provides additional data to the implantable device, allowing it to monitor and react to specific cardiac occurrences. The ECG provides more information than the EGM, which reading is typically available to an implantable device. For example, the implantable medical device can trigger off various portions of the cardiac cycle, rather than just the limited portion often available through an EGM. However, in order for an implantable device to record and monitor a pseudo ECG, the SVC electrode should be present and operable. Thus, in one embodiment, the present invention detects the presence and condition of the SVC electrode and enables the pseudo ECG function only when the functional integrity of the SVC electrode is confirmed.

In one embodiment, the invention provides an implantable medical device comprising a controller and pulse generator configured to deliver cardioversion pulses, a housing coupled with and containing the controller and pulse generator and acting as a can electrode, an SVC lead coupled with the controller and pulse generator and the housing, and a switch coupled between the SVC lead and the can electrode wherein the switch is controllable by the controller and electrically isolates the SVC lead from the can electrode when in an open position.

In another embodiment, the invention provides a method comprising providing a can electrode, a SVC lead electrically separable from the can electrode and a second lead electrically separated from the can electrode and the SVC lead, generating a pulse, and measuring the impedance between the can electrode and the SVC lead, between the can electrode and the second lead, and between the SVC lead and the second lead. The method further involves determining if the measured impedances are within a predetermined range, and classifying each of the can electrode, the SVC lead, and the second lead as operable or inoperable based on the determination of the measured impedances.

In yet another embodiment, the invention provides an implantable medical device for cardioversion and/or defibrillation, the implantable medical device comprising a can electrode, a SVC lead, and means for determining the operability of the SVC lead.

In another embodiment, the invention provides a method of utilizing an implantable medical device, the method comprising detecting the presence of an SVC lead that is electrically separable from a can electrode, setting the SVC lead to present once it is detected, measuring the impedance of the SVC lead, and determining if the SVC lead is operable based on the measured impedance.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 4 is a sample table illustrating the possible impedance measurements obtained for each of the can electrode, SVC electrode and RV electrode in the implantable medical device of FIG. 2 when a given electrode is inoperable.

DETAILED DESCRIPTION

The embodiments of the invention are preferably implemented in the context of an ICD system or a PCD system that may have single or dual chamber pacing and/or cardioversion/defibrillation capabilities of the types described in commonly assigned U.S. Pat. Nos. 5,549,642 and 5,755,742, both of which are incorporated herein by reference in their entireties.

Figure 1:
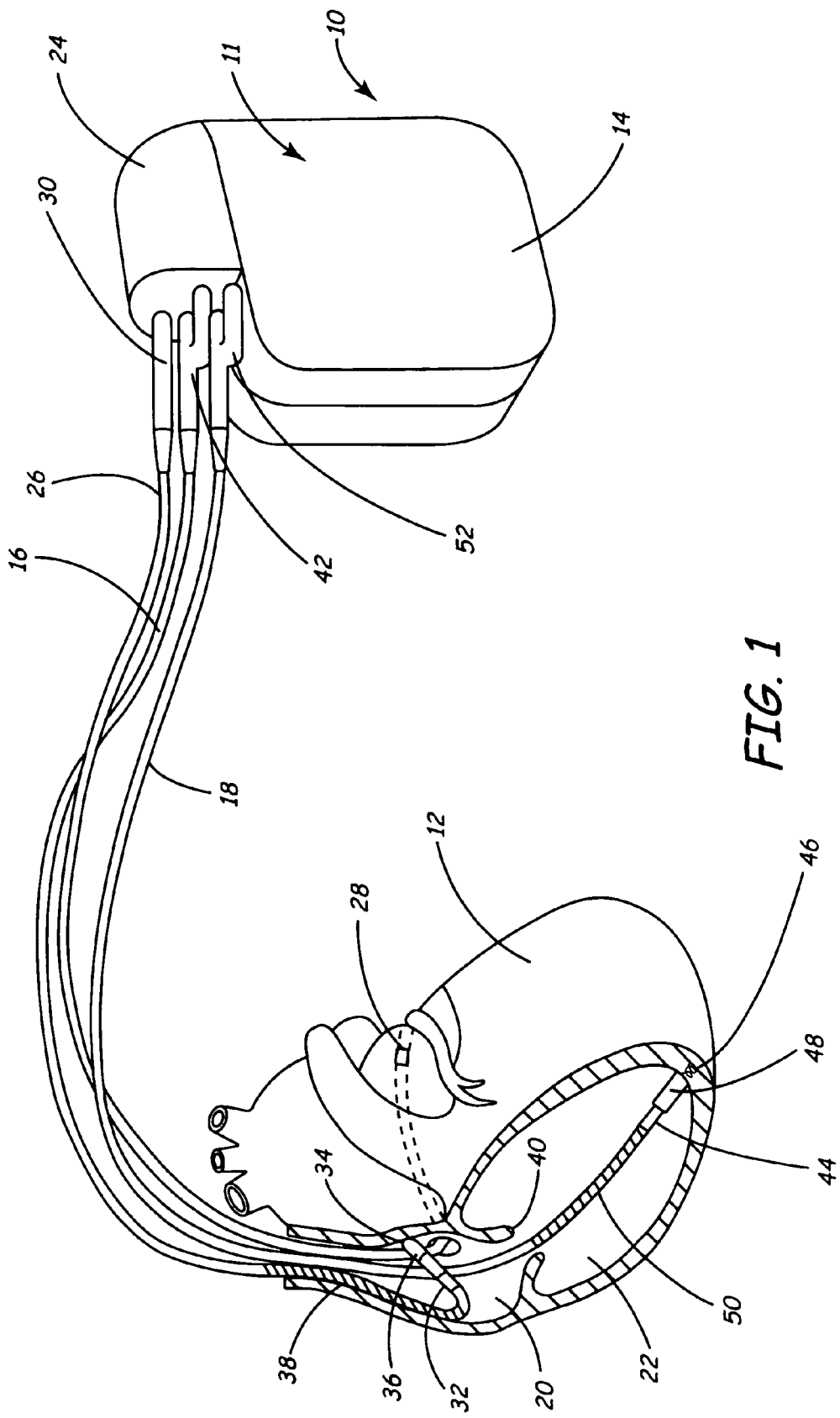
FIG. 1 is a partially sectional perspective view of an implantable medical device with a plurality of leads cooperating with a heart.

FIG. 1 illustrates a dual chamber, multi-programmable, implantable medical device (IMD) 10 and associated lead system for providing atrial and ventricular sensing functions, based on the programmed pacing and/or sensing mode and providing atrial or ventricular cardioversion therapies.

Depending upon the programmed pacing mode, pacing pulses may be applied to the atrium and/or ventricle in response to the detection of the appropriate bradycardia condition by the IMD 10. The pacing and sensing functions may be effected through atrial and ventricular bipolar pace/sense electrode pairs at the ends of right atrial/superior vena cava (RA/SVC) and right ventricular (RV) leads 16 and 18, respectively. Leads 16 and 18 may be fixed in the right atrium 20 and right ventricle 22, respectively, that are electrically coupled to the circuitry of IMD 10 through a connector block 24.

A coronary sinus (CS) lead 26 includes an elongated insulating lead body enclosing one elongated coiled wire conductor coupled to an elongated exposed coil wire CS cardioversion electrode 28. CS cardioversion electrode 28, illustrated in broken outline, is located within the coronary sinus of the heart 12. At the proximal end of CS lead 26 is a connector end 30 having an exposed connector coupled to the coiled wire conductor and attached within the connector block 24 to connector block terminals in a manner well known in the art.

The RA/SVC lead 16 may include an elongated insulating lead body carrying concentric, electrically isolated, coiled wire conductors separated from one another by tubular insulating sheaths. The lead body may be in an atrial J-shape in order to position its distal end in the right atrial appendage. An atrial pace/sense ring electrode 32 and an extendable helical, pace/sense electrode 34, mounted retractably within an insulating electrode head 36, are formed distally to the bend of the J-shape. Helical electrode 34 is extendable out of the electrode head 36 and can be screwed into the atrial appendage in a manner well known in the art.

RA pace/sense electrodes 32 and 34 are employed for atrial pacing and for near-field sensing of P-waves. An elongated, exposed coil, RA/SVC cardioversion electrode 38 is supported on RA lead 16 extending proximally to pace/sense ring electrode 32 and coupled to the third coiled wire conductor within the RA lead body. RA/SVC cardioversion electrode 38 preferably is 10 cm in length or greater and is configured to extend from within the SVC and toward the tricuspid valve 40. At the proximal end of the RA lead 16 is a bifurcated connector 42 which carries three exposed electrical connectors, each coupled to one of the coiled wire conductors, that are attached within the connector block 24 to connector block terminals in a manner well known in the art.

The delivery of atrial cardioversion/defibrillation therapies to the atria may be effected through selected combinations of intracardiac electrodes, e.g. the illustrated exemplary RA/SVC cardioversion electrode 38 and the CS cardioversion electrode 28. The exposed surface 11 of the outer housing or can of the IMD 10 may be selectively used as a can electrode 14. Can electrode 14 may serve as a subcutaneous remote cardioversion electrode in combination with one or more intracardiac cardioversion electrodes for cardioverting or defibrillating the atria.

The RV lead 18 may include an elongated insulating lead body, enclosing at least three concentric, electrically isolated, coiled wire conductors, separated from one another by tubular insulating sheaths. Located adjacent the distal end of the RV lead 18 are a pace/sense ring electrode 44, and a helical, pace/sense electrode 46, mounted retractably within an insulating electrode head 48. Helical electrode 46 is extendable out of the electrode head 48 and can be screwed into the ventricular apex in a manner well known in the art. RV pace/sense electrodes 44 and 46 are each coupled to a coiled wire conductor within the RV lead body and are employed for cardiac pacing in the ventricle and for sensing near-field R-waves.

In embodiments of the present invention, implemented to delivering ventricular cardioversion therapies, a distal segment of RV lead 18 also supports an elongated, exposed wire coil, cardioversion electrode 50. Cardioversion electrode 50 may be placed in the right ventricle 22 of heart 12 and connected to a further coiled wire conductor within the RV lead body. Although not specifically illustrated, it will be understood that the ventricular cardioversion therapies may be delivered between further RV cardioversion electrodes in combination with cardioversion electrode 50 or between the cardioversion electrode and the can electrode 14 and/or the CS cardioversion electrode 28 or the RA/SVC cardioversion electrode 38. At the proximal end of the RV lead 18 is a bifurcated connector end 52 having a plurality of electrical connectors, each coupled to one of the coiled conductors in the RV lead body, that are attached within the connector block 24 to connector block.

Figure 2:
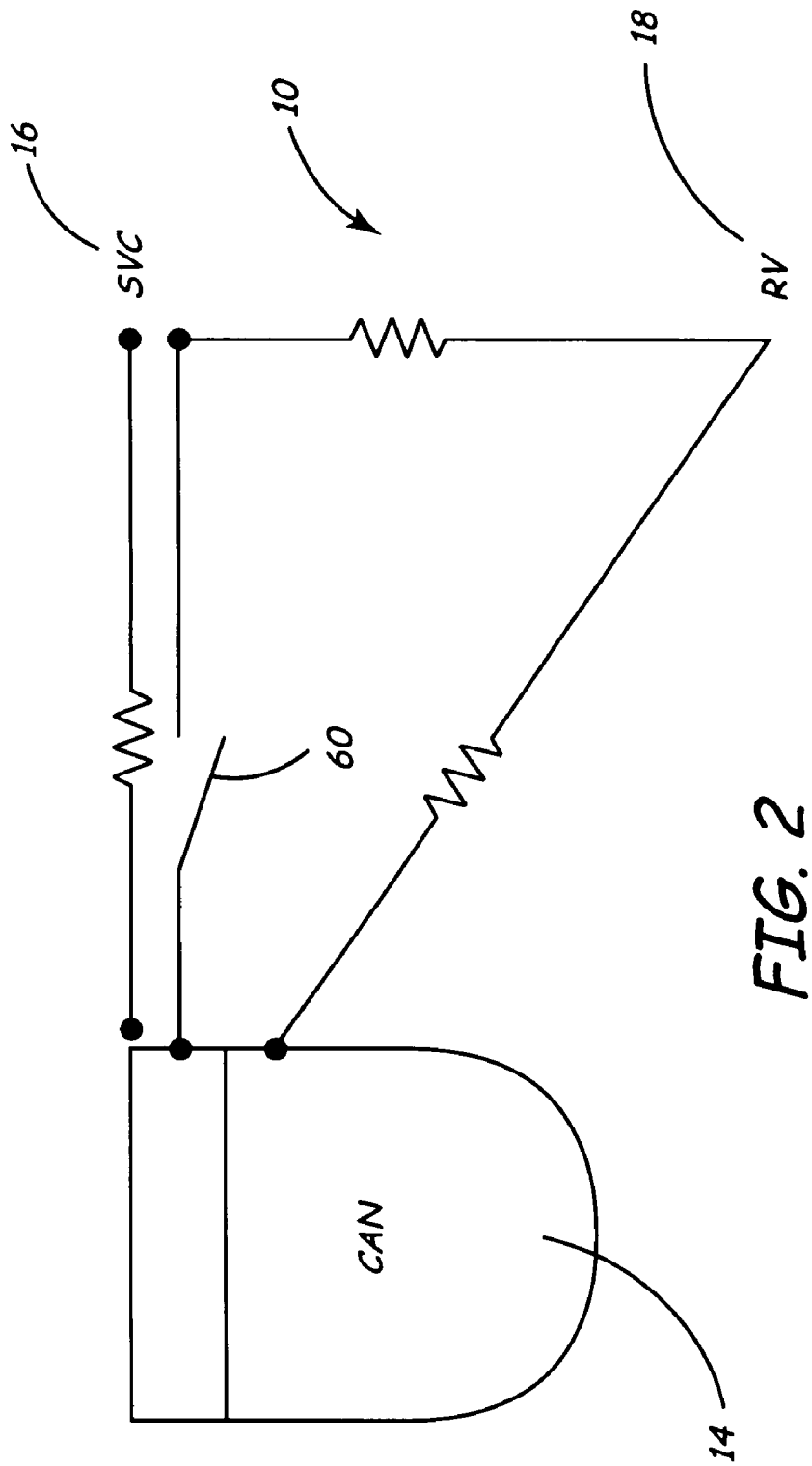
FIG. 2 is a schematic illustration of an implantable medical device having an active can electrode shown in conjunction with a RV electrode and a SVC electrode.

FIG. 2 is a schematic illustration of IMD 10. Can electrode 14 is illustrated with respect to SVC lead 16 and RV lead 18. Other leads may also be utilized, but are not illustrated. Typically, SVC lead 16 will be electrically connected to can electrode 14, thus rendering them electrically indistinguishable from one another. Switch 60 is provided to selectively electrically isolate can electrode 14 from SVC lead 16.

For various reasons, it may be desirable to verify the performance of the various leads coupled to IMD 10. To do so, pacer timing and control circuit 212 initiates a low voltage or "sub-threshold" discharge. The impedance across each pair of leads is then measured and compared with a predetermined standard. For example, it may be assumed that an operable lead should have an impedance of between about 20 Ω (ohms) to 200 Ω. If an impedance value outside of this range is measured, the lead may be classified as inoperable. The separate measurement of the impedance of can electrode 14 and SVC lead 16 is possible because can electrode 14 is electrically separable from SVC lead 16.

Figure 3:
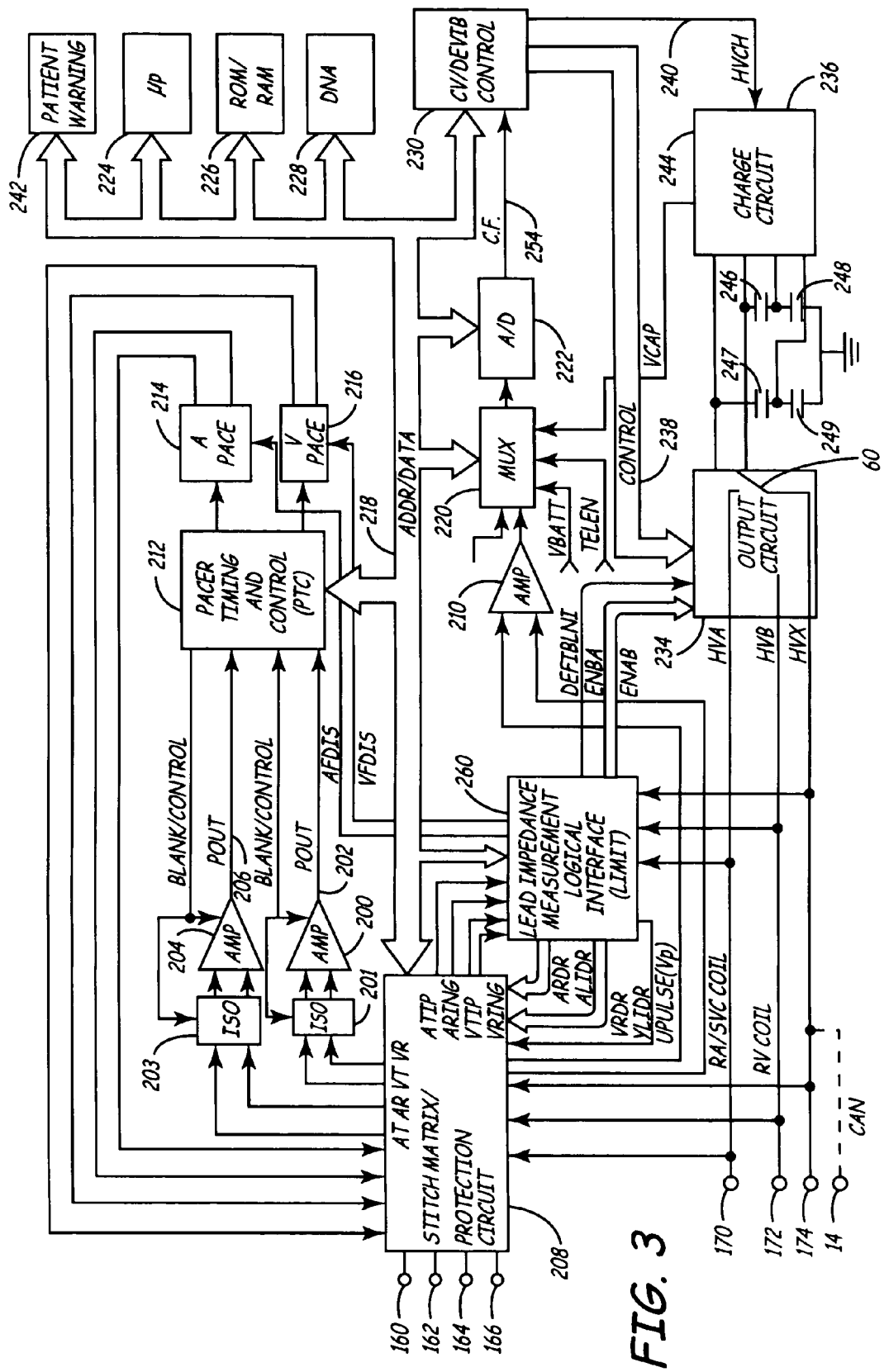
FIG. 3 is a functional schematic diagram of the circuitry of a comprehensive dual chamber, implantable pacemaker/cardioverter/defibrillator

FIG. 3 is a functional schematic diagram of the circuitry of IMD 10 in which the present invention may usefully be practiced. IMD 10 may be in the form of comprehensive dual chamber, implantable pacemaker/cardioverter/defibrillator (PCD). Certain of the pace/sense and cardioversion/defibrillation functions may be disabled or not provided to configure the PCD device to operate in other dual chamber or single chamber PCD operating modes. Therefore, FIG. 3 should be taken as exemplary of the circuitry of the type of IMD 10 in which the invention may be embodied, and not as limiting, as it is believed that the invention may usefully be practiced in a wide variety of device implementations.

The circuitry of FIG. 3 includes a high voltage section for providing relatively high voltage cardioversion/defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided in a manner well known in the art.

The block diagram of FIG. 3 depicts the atrial and ventricular pace/sense and cardioversion/defibrillation lead connector terminals of the connector block 24. Assuming the electrode configuration of FIG. 1, the correspondence to the illustrated leads and electrodes is as follows: can electrode 14 can be hard wired or programmably substituted for the defibrillation electrode terminal 174. Terminal 172 is adapted to be coupled through RV lead 18 to RV COIL electrode 50. Terminal 170 is adapted to be coupled through RA lead 16 to RA/SVC COIL electrode 38.

Terminals 164 and 166 are adapted to be coupled through lead 18 to RV pace/sense electrodes 44 and 46 for sensing and pacing in the ventricle. Terminals 160 and 162 are adapted to be coupled through lead 16 to RA pace/sense electrodes 32 and 34 for sensing and pacing in the atrium. Preferably, bipolar pace/sense electrodes are employed in the practice of the invention, but their configuration, fixation in contact with and positioning with respect to the atria and ventricles may differ from those shown in FIG. 1.

Terminals 170, 172 and can electrode 14 are coupled to high voltage output circuit 234. Terminal 170 and can electrode 14 may be electrically decoupled by opening switch 60. High voltage output circuit 234 includes high voltage switches controlled by CV/DEFIB Control logic 230 via control bus 238. The switches within circuit 234 control which electrodes are employed and which are coupled to the positive and negative terminals of the capacitor bank including a first capacitor pair 246 and 248 and a second capacitor pair 247 and 249 during delivery of the intermediate and high voltage cardioversion and defibrillation shocks. The output stage is provided with the two separate output capacitor banks 246, 248 and 247, 249 which are sequentially discharged during sequential shock defibrillation and simultaneously discharged during single or simultaneous shock defibrillation through a two or three defibrillation electrode system.

Terminals 164 and 166 are coupled through switch matrix and protection circuit 208 to the R-wave sense amplifier 200 through an input isolation circuit 201. R-wave sense amplifier 200 preferably takes the form of an automatic gain controlled amplifier providing an adjustable sensing threshold as a function of the measured R-wave signal amplitude. A VSENSE signal is generated on R-OUT line 202 whenever the signal sensed between the VTIP and VRING electrodes appearing at terminals 164 and 166 exceeds the current ventricular sensing threshold. Terminals 160 and 162 are similarly coupled through switch matrix and protection circuit 208 through an input isolation circuit 203 to the P-wave sense amplifier 204, which preferably also takes the form of an automatic gain controlled amplifier providing an adjustable sensing threshold as a function of the measured P-wave amplitude. An ASENSE signal is generated on P-OUT line 206 whenever the signal sensed between ATIP, ARING electrodes coupled to terminals 160, 162 exceeds the current atrial sensing threshold. The APACE and VPACE output circuits 214 and 216 are also coupled to terminals 160, 162 and 164, 166, respectively. The atrial and ventricular sense amplifiers 204 and 206 are isolated from the APACE and VPACE output circuits 214 and 216 by appropriate isolation and blanking circuitry in each sense amplifier 204, 200 and the associated input isolation circuits 203, 201 operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5,117,824, incorporated herein by reference in its entirety.

Switch matrix and protection circuit 208 is also used in an EGM sensing mode to select which of the available pace/sense electrodes are coupled to wide band (0.5-200 Hz) EGM sense amplifier 210 for use in digital signal storage and analysis of the patient's atrial and ventricular EGM. The selection of the terminals 160, 162 and 164, 166 is controlled by the microprocessor 224, via data/address bus 218, in order to apply atrial and ventricular signals to the bandpass amplifier 210. Output signals from bandpass amplifier 210 are provided to multiplexer 220, and thereafter converted to multi-bit digital signals by A/D converter 222, for storage in RAM in ROM/RAM 226 under control of DMA 228. Microprocessor 224 may employ digital signal analysis techniques to characterize the digitized signals stored in ROM/RAM 226 to recognize and classify the patient's heart rhythm employing any of the numerous signal processing methodologies known to the art.

The circuitry of FIG. 3 may provide atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the pacer timing and control (PTC) circuitry 212 includes programmable digital counters which control the basic time intervals associated with bradycardia pacing modes including DDD, VVI, DVI, VDD, AAI, DDI and other modes of single and dual chamber pacing well known to the art.

Isolation circuits 203 and 201 operate to disconnect the input terminals of atrial and ventricular sense amplifiers 204 and 200 from the APACE and VPACE output circuits 214 and 216 on time-out of the atrial and ventricular escape intervals for a short time under the control of the PTC circuitry 212 in a manner well known in the art. Blanking of the atrial and ventricular sense amplifiers 204 and 200 is also provided by PTC circuitry 212 in accordance with the conventional practice. Although not shown in FIG. 3, it will be understood that high voltage protection power FETs are incorporated within switch matrix and protection circuit 208 between the atrial and ventricular pace/sense terminals, 160, 162 and 164, 166 and the APACE and VPACE output circuits 214 and 216, respectively, to protect against IC damage from cardioversion/defibrillation shock energy induced across the electrodes of the pace/sense leads when such shocks are delivered.

In the event that generation of a cardioversion or defibrillation shock is required, microprocessor 224 employs the an escape interval counter to control timing of such cardioversion and defibrillation shocks, as well as associated refractory periods. In response to the detection of atrial or ventricular fibrillation or tachyarrhythmia requiring a cardioversion shock, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors 246-249 is monitored via VCAP line 244, which is passed through multiplexer 220. In response to reaching a predetermined value set by microprocessor 224, the voltage on VCAP line 244 results in generation of a logic signal on Cap Full (CF) line 254, terminating charging. Thereafter, timing of the delivery of the defibrillation or cardioversion shock is controlled by PTC circuitry 212. Following delivery of the shock therapy, the microprocessor 224 may then return the operating mode to cardiac pacing and awaits the next successive interrupt due to pacing or the occurrence of a sensed atrial or ventricular depolarization.

In the illustrated operating system, delivery of the cardioversion or defibrillation shocks is accomplished by output circuit 234, under control of control circuitry 230 via control bus 238. Output circuit 234 determines whether a monophasic or biphasic shock is delivered, the polarity of the electrodes and which electrodes are involved in delivery of the shock. Output circuit 234 also includes high voltage switches which control whether electrodes are coupled together during delivery of the shock. Alternatively, electrodes intended to be coupled together during the shock may simply be permanently coupled to one another, either exterior to or interior of the device housing, and polarity may similarly be preset, as in current implantable defibrillators. An example of output circuitry for delivery of biphasic shock regimens to multiple electrode systems may be found in U.S. Pat. No. 4,727,877, incorporated by reference in its entirety.

Turning to the lead integrity test operations of the present invention, a lead impedance measurement logical interface (LIMLI) 260 is provided and employed in a test mode initiated by commands from the microprocessor 224 on address/data bus 218 either automatically on a periodic basis or in response to a programmed-in command received through telemetry. Very generally, when the lead impedance test mode is initiated by microprocessor 224, a "force" terminal pair and a "measure" terminal pair having only the lead under test in common are selected from among defibrillation terminals 170, 172 and 174/14 and pace/sense terminals 160, 162 and 164, 166 (through connections made in switch matrix and protection circuit 208 and output circuit 234 as described below). In the following description, the term "lead" comprises a single electrode and lead conductor having a proximal connector element for connection to one of these terminals, even though it may be part of a bipolar or tripolar pacing or cardioversion/defibrillation lead as described above, and includes the can electrode 14 and associated electrical connections between it an terminal 174. The "lead impedance" as further defined below includes the intrinsic lead resistive impedance that may be measured between the distal electrode and the proximal connector element when the lead is not implanted. This intrinsic lead impedance is a relatively low value for a lead without any insulation defects or loose or open internal connections with the proximal connector element and the distal electrode. The lead impedance that is actually measured when the lead is implanted includes the electrode/tissue interface impedance (ETI), and also includes any impedance caused by a loose or otherwise poor electrical connection of the proximal lead connector element with the IPG connector block connector element. The ETI impedance may be considered a resistive impedance, for purposes of the lead integrity test and varies depending on electrode surface area/shape and associated current density. The total normal lead impedance value ranges for any particular lead design and combinations of excitation and measure lead pairs may be derived empirically from clinical experience gained over time.

A sub-threshold, excitation or "force", lead impedance voltage pulse (LIPULSE or $V_p$) of predetermined amplitude and pulse width is generated by a force pulse generator within LIMLI 260. The sub-threshold pulse is set at a value that has insufficient energy to capture the heart. The force pulse $V_p$ is applied to the terminal of the force terminal pair not coupled to the lead under test (the "driven terminal") while the terminal of the lead under test is held at system ground. The excitation path therefore is through the driven terminal, the lead not under test, the patient's body and/or heart tissue, the lead under test, and system ground. A measure path is also selected which includes a measure terminal different from the driven terminal, the lead coupled thereto, the patient's body and/or heart tissue, the lead under test and its terminal at system ground. It should be noted that the force pulse $V_p$ could be in the form of a current pulse instead of a voltage pulse, and, in either case, may consist of one or more phases of differing polarity. For simplicity, the force pulse $V_p$ is assumed to be a constant voltage pulse.

The electrical current delivered to the excitation path during the delivery of the force pulse $V_p$ is measured as a signal $I_m$ in the LIMLI 260. At the same time, the voltage appearing across the measure terminal pair is measured as the signal $V_m$ in LIMLI 260. The measure and force terminal pairs have the lead under test in common, and no current flows through the lead coupled to the measure terminal. From the measured current $I_m$ flowing into the excitation path and the measured voltage $V_m$ induced across the measure path between the measure terminal pair, it is possible to calculate the apparent impedance of the lead under test and infer the state of lead integrity by comparison to maximum and minimum impedance threshold values. If the calculated impedance is within the acceptable impedance range, the lead under test may be assumed to not have a lead integrity failure. However, since the excitation path and the measure path include the two other leads, a further diagnosis of the lead impedances obtained after concluding lead integrity tests of all of the involved leads may be necessary to determine which lead exhibits a lead integrity failure.

Very generally, in one approach illustrated in FIG. 3, the measured current $I_m$ and voltage $V_m$ are employed to derive a lead impedance in microprocessor 224 that is then employed by the microprocessor 224 in a diagnostic comparison to normal impedance values in order to diagnose tentative lead integrity failures. The impedance thresholds for the particular leads under test are derived in advance from characteristics of the lead type or model under test and stored in RAM/ROM 226 for use by the microcomputer 224. When a lead impedance failure is tentatively diagnosed from the comparison, a patient warning is invoked in patient perceptible warning device 242 to alert the patient to contact the attending medical personnel.

Whether or not a lead integrity failure is diagnosed by microcomputer 224, the impedance data may also be stored in RAM in ROM/RAM 226 until telemetry out is initiated. The impedance data may be collected on a regular schedule and be stored with related data for later telemetry out. The stored data may be compressed, for example as weekly high and low impedance values, and retained for extended periods of time. When telemetered to the external programmer, they may be displayed by the external programmer and interpreted by the physician with assistance of a programmer-resident lead impedance thresholds and an analysis program to display lead impedance trends and diagnose potential faulty lead insulation or lead conductor fractures involving all the potential lead integrity failure combinations of a unipolar, bipolar or tripolar lead. Alternatively, LIMLI 260 may apply a test pulse directly to the lead under test and in a similar fashion, measure the impedance values.

FIG. 4 illustrates the results of impedance measurements made across a given pair of leads when a given electrode is inoperable. For example, if can electrode 14 is inoperable, impedance measurements from SVC 16 to can electrode 14 and from can electrode 14 to RV lead 18 will both be out of range. At the same time, however, impedance measurements from SVC lead 16 to RV electrode 18 may be within the predetermined range. Similarly, if RV lead 18 is inoperable, measurements from SVC lead 16 to RV lead 18 and can electrode 14 to RV lead 18 will be out of range. Measurements across SVC lead 16 and can electrode 14 may be within the predefined range. If SVC lead 16 is inoperable or problematic, impedance measurements across SVC lead 16 and can electrode 14 and measurements across SVC lead 16 and RV lead 18 will be out of range. Measuring the impedance across can electrode 14 and RV lead 18 will provide an in range reading. Thus, it is possible to measure impedance across these three leads and determine if they are functioning properly. Of course, additional leads could also be measured in a similar fashion.

While the foregoing discussion relates to a sub-threshold lead impedance test, it will be understood that any other type of impedance measurement known in the art may be used within the context of the current invention. For example, any type of mono-phasic or bi-phasic type pulse could be applied as the test signal. An alternating current (AC) signal could be applied to derive an AC impedance measurement, for instance. In another embodiment, impedance may be measured by delivering a low-energy defibrillation pulse between two of the electrodes, although this method is not preferred as it will result in some patient discomfort. Thus, the specific impedance mechanism described in detail above should be considered exemplary only.

If a given lead is determined to be inoperable, control logic 230 can reconfigure the defibrillation and cardioversion pathways. For example, if SVC lead 16 is determined to be inoperable, control logic 230 may exclude it and include can electrode 14 in its place. In this manner, the patient will continue to be able to receive therapy, despite a detected malfunction in one of the leads. In addition to reconfiguring the pathways, an alarm or indication may be provided to alert the patient, a physician, or an attendant to the condition. When examined by a cardiologist or other medical caregiver, data stored within a memory of IMD 10 can indicate the failure of a given lead and can also provide the history of that lead over a given period of time.

IMD 10 can measure the intrinsic electrical activity of heart 12 by measuring across any given pair of sensing leads, e.g., sense leads 34, 46. However, the data obtained is limited to only a portion of the cardiac electrical cycle and is referred to as an EGM (electrogram). The present invention, by electrically separating can electrode 14 from SVC lead 16, allows a pseudo ECG (electrocardiogram) to be taken. This provides more complete data about the cardiac electrical cycle and allows for more precise delivery of pacing or cardioversion pulses. That is, IMD 10 can monitor P waves, T waves, and the QRS complex rather than just a portion of that data normally detectable with an EGM. Thus, therapy can be timed and delivered synchronously with various portions of the cardiac cycle. Additionally, this data can be recorded over time and output for review by a cardiologist.

Figure 5:
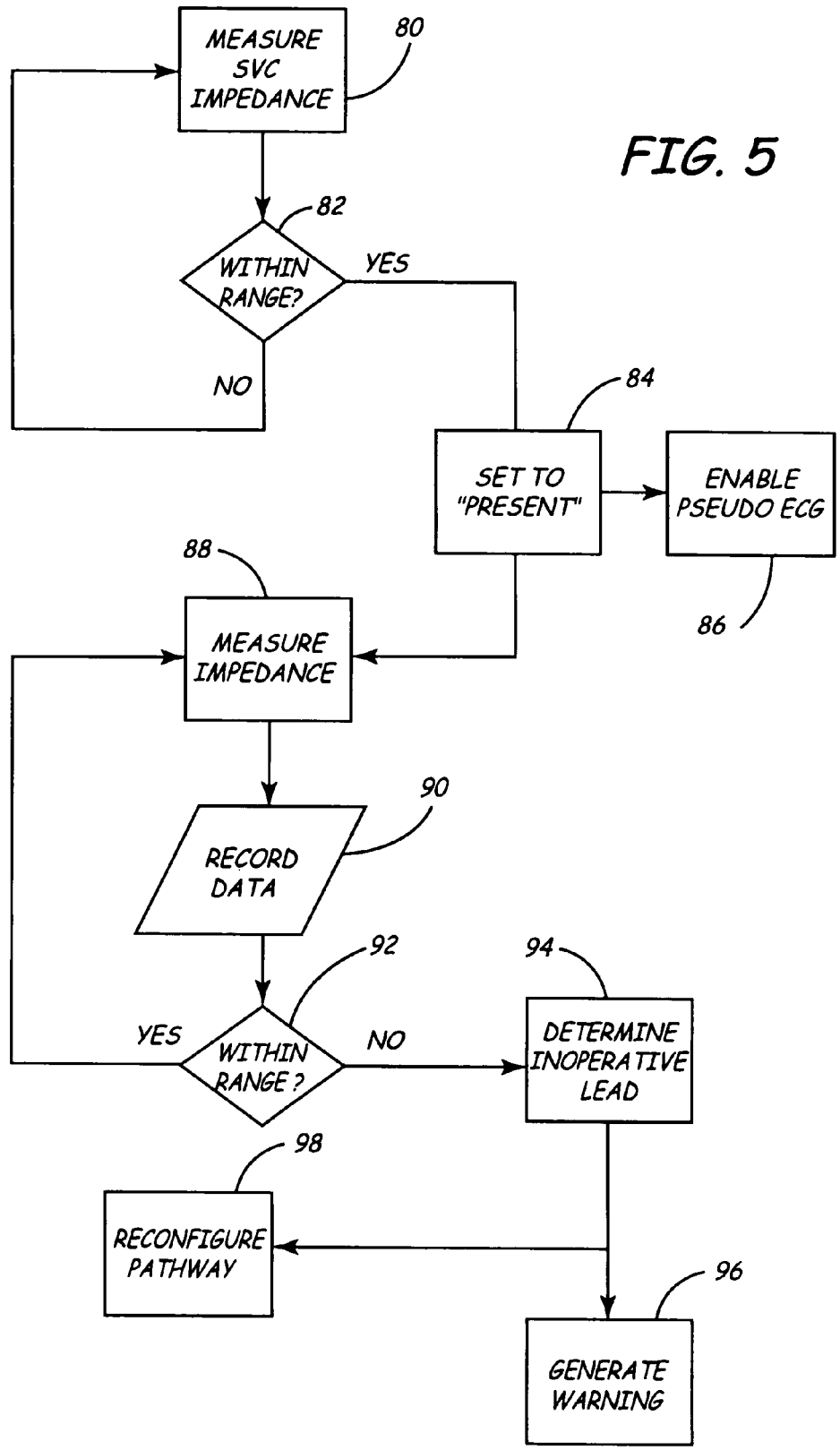
FIG. 5 is a flowchart illustrating the process of the implantable medical device of FIG. 2 in initially detecting and subsequently monitoring a SVC lead.

FIG. 5 is a flowchart illustrating a process of detecting and utilizing SVC lead 16. As explained above, SVC lead 16 may not always be implanted with IMD 10. Thus, IMD 10 should monitor for SVC lead 16 and only enable various functions that make use of the SVC lead once it is properly detected. At a periodic interval such as once per day, IMD 10 will attempt to measure the impedance of SVC lead 16, as illustrated in step 80. Assuming it is not present, the impedance value will always be extremely high and out of range. It will therefore be assumed that the lead is not present in the system, as shown by step 82.

Once SVC lead 16 has been connected (either with the initial implantation or subsequently), the impedance measurement will result in an impedance reading that is within the predetermined range. Once so detected, the SVC lead 16 is indicated as being "present" within the system, as depicted in step 84. Thereafter, IMD 10 will always assume the presence of SVC lead 16 until or unless it is externally reset. Also, once the SVC lead is found to be present, IMD 10 will enable the pseudo ECG functions that are dependent upon SVC lead 16 being present. This is illustrated in step 86. Subsequently, control circuit 230 can open switch 60 and measure between SVC lead 16 and can electrode 14, thus obtaining pseudo ECG data that may then be used appropriately.

Once SVC lead 16 is found to be present, the impedance of that SVC lead 16 and the other leads will be periodically measured to determine if they are operable, as indicated in step 88. Of course, this test could have been done on the other leads prior to initially detecting SVC lead. This test is performed by measuring across each pair of leads while a sub-threshold pulse is generated. In order to electrically distinguish can electrode 14 from SVC lead switch 60 should be opened. The data is recorded in step 90 so that a history for each measured lead can be developed. If the impedance measurements are all within the acceptable range in 92, the leads are determined to be operable and the measurement is repeated again in step 88 at the predetermined interval. For example, the test may be performed daily with little perceptible drain on battery performance.

If one or more of the measurements is out of range, IMD 10 will determine in step 94 which lead/electrode is inoperative. If appropriate, a warning may be generated in step 96 to alert the patient that a problem exists. Such a warning may be in the form of an audible tone or other appropriate warning indicia. If the inoperable lead is can electrode 14 or SVC electrode 16, the pseudo ECG function may then be disabled.

Once it has been determined that one or more leads is inoperative in step 94, control logic 230 may reconfigure the defibrillation and/or cardioversion pathways. That is, the inoperative lead will no longer be relied on. The remaining operative leads will be selectively utilized as appropriate. The energy output for a give pulse can likewise be modified so as to provide the optimum charge for the pathway selected.

While the current invention is described in terms of an SVC coil that may be selectively switched in common with the IMD can, many other types of electrodes may be provided in place of the SVC coil to provide all of the capabilities and advantages described herein. For example, an electrode positioned within the coronary sinus such as CS cardioversion electrode 28 may be substituted for the SVC coil within the context of the current invention. Alternatively, a subcutaneous patch electrode may be utilized for this purpose. In another embodiment, the RV electrode could be selectively coupled to the can such that a defibrillation shock is delivered between the can/RV electrode and the SVC electrode. Any other types of high-voltage electrode positioned in another area of the body could be substituted for the SVC coil electrode, if desired.

According to yet another aspect of the invention, multiple high-voltage electrodes may be provided on a single lead, with the device having the capability to selectively couple one or more such electrodes in common with the can.

Figure 6:
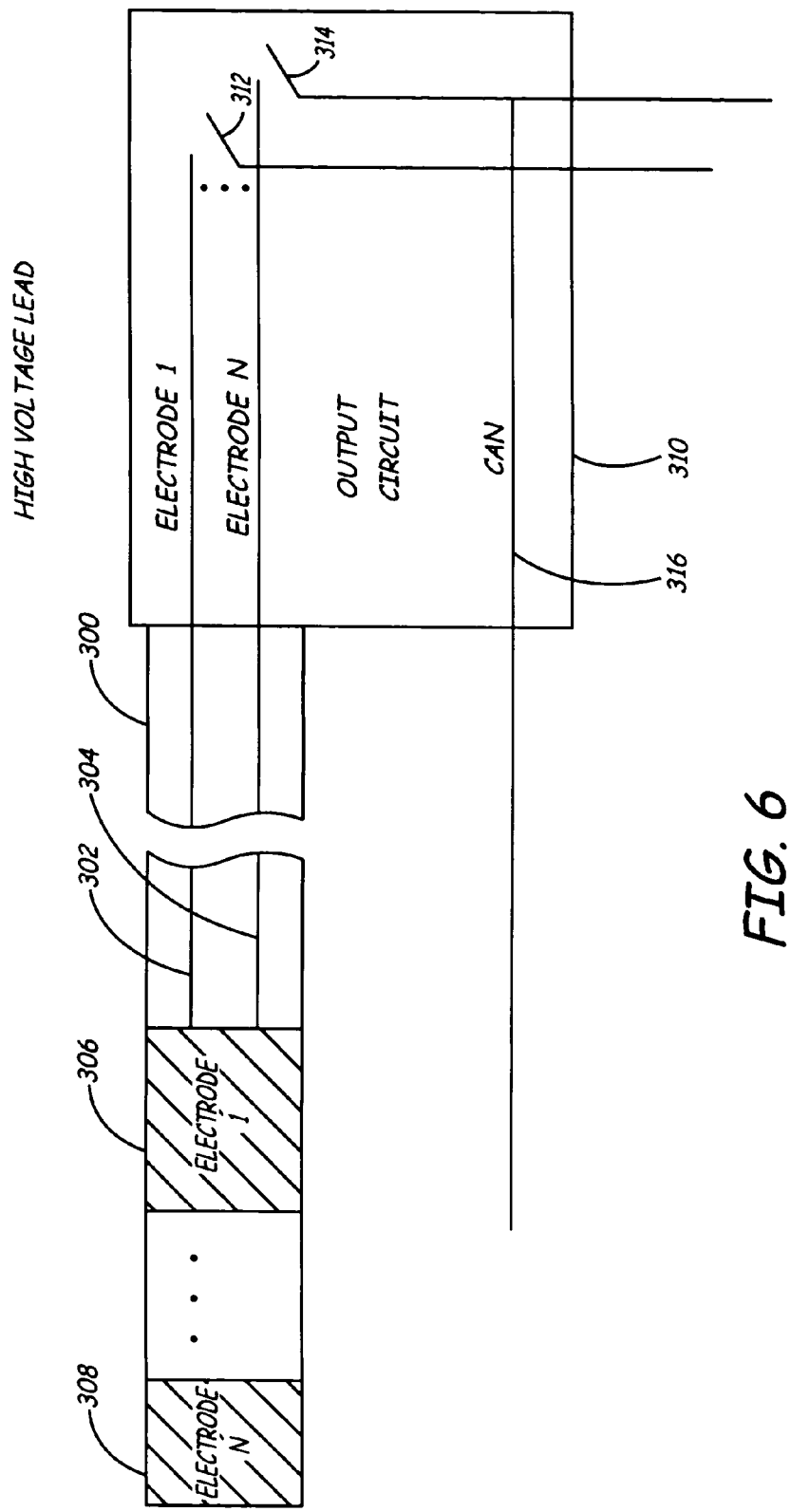
FIG. 6 is a block diagram of an embodiment of the invention that utilizes multiple high-voltage electrodes carried on a single lead.

FIG. 6 is block diagram of an embodiment utilizing multiple high-voltage coil electrodes carried on a single lead. In this embodiment, lead 300 carries multiple conductors 302 and 304, each coupled to a respective high voltage electrode 306 and 308. Although only two electrodes and conductors are shown, it will be understood any number of such electrodes and conductors may be provided. Lead 300 is coupled to output circuit 310, which corresponds to output circuit 234 of FIG. 3. In this embodiment, output circuit 310 includes respective switches 312 and 314 for each of the conductors 302 and 304. Either or both of these conductors may be selectively coupled to the can electrode 316. In this manner, a high-voltage shock may be delivered using one or more of the electrodes of lead 300 and/or the can electrode 316. Any combination of these electrodes may be utilized based on impedance measurements made in a manner similar to that discussed above. The use of a particular electrode configuration can further be selected based on measured DFT thresholds, on the unique anatomy of a given patient, and on other patient-specific considerations that may be determined by a physician and retained for later use within a storage device of the IMD.

A number of embodiments of the present invention have been described. Nevertheless, it will be understood that various modifications may be made without departing from the spirit and scope of the invention. Accordingly, other embodiments are within the scope of the following claims. For example, the present invention can monitor the status of the various leads with or without providing the ability to make pseudo ECG measurements. Likewise, the SVC lead can be assumed to be present if so desired, eliminating the initial detection of that lead.

What is claimed is:

1. A method for use in an Implantable Medical Device (IMD), wherein the IMD includes a housing functioning as a can electrode, comprising:
   coupling a high-voltage lead to the can electrode;
   coupling a second lead to the can electrode;
   selectively electrically coupling and decoupling the high-voltage lead from the can electrode;
   measuring a first impedance between the can electrode and the high-voltage lead in response to the can electrode and the high-voltage lead being electrically coupled; and
   determining whether the high-voltage lead is present in response to the first impedance and enabling a non-therapy related function dependent upon the high-voltage lead being present.

2. The method of claim 1, wherein the enabling a non-therapy related function comprises generating cardiac cycle data via the high voltage lead and the can electrode in response to the high voltage lead being present and via other than the high voltage lead and the can electrode in response to the high voltage lead not being present.

3. An implantable medical device (IMO) comprising:
a control circuit;
a housing coupled with the control circuit and acting as a can electrode;
a first lead coupled with the control circuit and the housing;
a second lead coupled to the housing;
a switch coupled between the first lead and the can electrode, wherein the control circuit controls the switch to selectively decouple the first lead from the can electrode; and
an impedance measurement circuit measuring a first impedance between the can electrode and the first lead in response to the control circuit electrically coupling the can electrode and the first lead, wherein the control circuit determines the first lead is present in response to the first impedance and enables a non-therapy related function dependent upon the first lead being present, wherein the impedance measurement circuit measures a second impedance between The second lead and the can electrode and a third impedance between the first lead and the second lead, and the control circuit includes means for determining if one of the can electrode, the first lead and the second lead is inoperable based on the measured impedance, and wherein, in response to one of the can electrode, the first lead and the second lead being inoperable, the control circuit isolates the one of the can electrode, the first lead and the second lead from a predetermined cardioversion pathway.

4. The IMD of claim 3, wherein the control circuit includes circuits to deliver a sub-threshold pulse.

5. The IMD of claim 4, wherein the first lead is selected from the group consisting of an SVC lead, an RV lead, a coronary sinus lead, and a subcutaneous lead.

6. The IMD of claim 4, wherein one of the first lead and the second lead is determined operable if the measured impedance is between about 20–200 ohms.

7. The IMD of claim 4, wherein the control circuit determines whether the first lead is operable in response to the first impedance and includes circuits to disable the first lead when the first lead is determined to be inoperable.

8. The IMD of claim 4, wherein the control circuit includes circuits to disable the first lead prior to the control circuit determining that the first lead is present.

* * * * *

UNITED STATES PATENT AND TRADEMARK OFFICE
CERTIFICATE OF CORRECTION

| | |
|---|---|
| PATENT NO. | : 7,050,851 B2 |
| APPLICATION NO. | : 09/897859 |
| DATED | : May 23, 2005 |
| INVENTOR(S) | : William J. Piombon et al. |

It is certified that error appears in the above-identified patent and that said Letters Patent is hereby corrected as shown below:

Col. 13, line 1, please delete "device (IMO)" and insert --device (IMD)--.

Col. 14, line 9, please delete "claim 4" and insert --claim 3--.

Col. 14, line 12, pelase delete "claim 4" and insert --claim 3--.

Col. 14, line 15, please delete "claim 4" and insert --claim 3--.

Col. 14, line 22, please delete "claim 4" and insert --claim 3--.

Signed and Sealed this

Twenty-sixth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,050,851 B2
APPLICATION NO. : 09/897859
DATED : May 23, 2006
INVENTOR(S) : William J. Piombon et al.

It is certified that error appears in the above-identified patent and that said Letters Patent is hereby corrected as shown below:

Col. 13, line 1, please delete "device (IMO)" and insert --device (IMD)--.

Col. 14, line 9, please delete "claim 4" and insert --claim 3--.

Col. 14, line 12, pelase delete "claim 4" and insert --claim 3--.

Col. 14, line 15, please delete "claim 4" and insert --claim 3--.

Col. 14, line 22, please delete "claim 4" and insert --claim 3--.

This certificate supersedes Certificate of Correction issued December 26, 2006.

Signed and Sealed this

Thirtieth Day of January, 2007

JON W. DUDAS
*Director of the United States Patent and Trademark Office*